(12) United States Patent
Schneider et al.

(10) Patent No.: US 7,739,912 B2
(45) Date of Patent: Jun. 22, 2010

(54) ULTRASONIC FINGERPRINT SCANNING UTILIZING A PLANE WAVE

(75) Inventors: John K. Schneider, Snyder, NY (US); Jack C. Kitchens, Tonawanda, NY (US); James T. Baker, Lockport, NY (US)

(73) Assignee: Ultra-Scan Corporation, Amherst, NY (US)

( * ) Notice: Subject to any disclaimer, the term of this patent is extended or adjusted under 35 U.S.C. 154(b) by 429 days.

(21) Appl. No.: 11/245,883

(22) Filed: Oct. 7, 2005

(65) Prior Publication Data

US 2007/0258628 A1    Nov. 8, 2007

Related U.S. Application Data

(60) Provisional application No. 60/616,953, filed on Oct. 7, 2004.

(51) Int. Cl.
*G01N 29/00* (2006.01)
*G06K 9/00* (2006.01)

(52) U.S. Cl. .............................. 73/620; 73/603; 73/622; 382/124

(58) Field of Classification Search ................... 73/620, 73/621, 622, 603; 600/445, 459, 437; 382/124; 356/171
See application file for complete search history.

(56) References Cited

U.S. PATENT DOCUMENTS

| | | | |
|---|---|---|---|
| 4,395,652 A * | 7/1983 | Nakanishi et al. ............ 310/334 |
| 4,718,421 A * | 1/1988 | Rohwedder et al. ............ 601/4 |
| 4,977,601 A | 12/1990 | Bicz |
| 5,177,353 A | 1/1993 | Schiller |
| 5,483,963 A | 1/1996 | Butler et al. |
| 5,551,295 A | 9/1996 | Stockburger |
| 5,563,345 A | 10/1996 | Kersten et al. |
| 5,647,364 A * | 7/1997 | Schneider et al. ............ 600/445 |
| 5,737,439 A | 4/1998 | Lapsley et al. |
| 6,078,265 A | 6/2000 | Bonder et al. |
| 6,219,439 B1 | 4/2001 | Burger |
| 6,310,371 B1 | 10/2001 | Hung |
| 6,317,508 B1 | 11/2001 | Kramer et al. |
| 6,552,841 B1 | 4/2003 | Lasser et al. |
| 6,628,377 B1 | 9/2003 | Sabatini et al. |
| 6,720,712 B2 | 4/2004 | Scott et al. |
| 6,812,621 B2 | 11/2004 | Scott |
| 6,971,991 B2 | 12/2005 | Lasser et al. |
| 2003/0156740 A1 | 8/2003 | Siegel et al. |

(Continued)

OTHER PUBLICATIONS

International Search Report For PCT/US05/36219, May 8, 2007, Ultra-Scan Corporation.

*Primary Examiner*—J M Saint Surin
(74) *Attorney, Agent, or Firm*—Hodgson Russ LLP

(57) ABSTRACT

The invention may be embodied as a fingerprint scanner having an ultrasonic wave detector, a platen, an ultrasonic wave generator located between the detector and the platen. The invention may be embodied as a method of scanning a finger. One such method includes providing a platen, a detector and a generator, the generator being placed between the platen and the detector. A finger may be provided on the platen, and an ultrasound wave pulse may be sent from the generator toward the finger. The wave pulse may be reflected from the finger, and received at the detector. The received wave pulse may be used to produce an image of the finger.

74 Claims, 16 Drawing Sheets

U.S. PATENT DOCUMENTS

| | | |
|---|---|---|
| 2003/0158819 A1 | 8/2003 | Scott |
| 2003/0229506 A1 | 12/2003 | Scott et al. |
| 2003/0229811 A1 | 12/2003 | Siegel et al. |
| 2004/0140735 A1 | 7/2004 | Scott et al. |
| 2005/0063571 A1 | 3/2005 | Setlak et al. |
| 2005/0063572 A1 | 3/2005 | Setlak et al. |
| 2005/0063573 A1 | 3/2005 | Setlak et al. |
| 2005/0089203 A1 | 4/2005 | Setlak |
| 2005/0094855 A1 | 5/2005 | Proano et al. |
| 2005/0105784 A1 | 5/2005 | Nam |
| 2005/0123176 A1 | 6/2005 | Ishii et al. |
| 2005/0141048 A1 | 6/2005 | Mizutani |
| 2005/0163353 A1 * | 7/2005 | Schneider et al. ........... 382/124 |
| 2006/0173316 A1 * | 8/2006 | Schneider et al. ........... 600/437 |

* cited by examiner

ULTRASONIC FINGERPRINT SCANNING UTILIZING A PLANE WAVE

CROSS-REFERENCE TO RELATED APPLICATION

This application claims the benefit of priority to U.S. provisional patent application Ser. No. 60/616,953, filed on Oct. 7, 2004.

FIELD OF THE INVENTION

The present invention relates to ultrasonic biometric readers, such as fingerprint scanners.

BACKGROUND OF THE INVENTION

Since the 1800's fingerprint information has been collected from human fingers and hands by means of ink and paper. For the purposes of this document, the term "fingerprint" is used to mean the skin surface friction ridge detail of a portion of a hand, such as a single fingerprint, or the entire hand. In recent years various electronic fingerprint scanning systems have been developed utilizing optical, capacitance, direct pressure, thermal and ultrasonic methods. Methods based on ultrasound have proven to be highly accurate, since they are insulated from the effects of grease, dirt, paint, ink and other image contaminants.

In an ultrasonic system, a piezoelectric transducer may be used to send an ultrasonic wave through an ultrasound transmitting media. The dimensions of prior art ultrasonic scanners and the ultrasound emitters used in those prior art scanners are such that the emitter produces a wave that emanates from a small location, and therefore, the emitters used in the prior art devices may be thought of as point sources of the ultrasound energy.

In ultrasonic fingerprint scanners, the ultrasound wave is started and stopped to produce a pulse. At each material interface encountered by the pulse, a portion of the pulse reflects. For example, the interface between a platen and skin or the interface between air and skin may each reflect a portion of the pulse. The fraction of ultrasound reflected is a function of differences in impedance between the two materials comprising the interface. The fraction of ultrasound reflected can be calculated by the equation, $R=((Z_1-Z_2)/(Z_1+Z_2))^2$, where R is the fraction of sound reflected, $Z_1$ is the acoustic impedance of the first material and $Z_2$ is the acoustic impedance of the second material. Acoustic impedance is a measure of a material's resistance to the propagation of ultrasound. Acoustic impedance, Z, is defined as $Z=r\cdot c$, where r is the material density, and c is the longitudinal propagation velocity of ultrasound in the material. The larger the change in acoustic impedance, the larger the fraction reflected.

The reflected wave pulses may be detected by a detector. The elapsed time during which the pulse traveled from the ultrasound pulse emitter to the interface and back may be determined. The elapsed time may be used to determine the distances traveled by the pulse and its reflected wave pulses. By knowing the distance traveled, the position of an interface may be determined.

There may be many interfaces encountered by the emitted pulse, and so there may be many reflected wave pulses. Since it is the interfaces associated with a finger that are of interest in generating an image of a fingerprint, it may be necessary to identify those reflected wave pulses that are associated with the finger. The approximate position of a finger being scanned may be known, and therefore the pulse reflected from the finger may be expected during a particular time interval. In a technique commonly referred to as "range gating", a detector may be configured to ignore reflected pulses that are not received during that time interval. The reflected signals associated with the finger may be processed and converted to a digital value representing the signal strength. The digital value may be used to produce a graphical display of the signal strength, for example by converting the digital values to a gray-scale bitmap image, thereby producing a contour map of the finger surface which is representative of the depth of the ridge structure detail.

Although using ultrasound to produce an image of a fingerprint may be superior in detail to a similar image collected by an optical system or other means, existing ultrasound systems have deficiencies. Collecting information using an ultrasound transducer is usually accomplished by moving the ultrasound transducer side-to-side while advancing the transducer in a direction that is different from the side-to-side motion. Such an arrangement is commonly referred to as a raster scanning process. As the raster scanning process proceeds, the ultrasound raster scanning mechanism collects each pixel of image information individually, and records those pixels for use in generating an image of the fingerprint. The time required to collect a raster scanned ultrasonic image may be longer than the time needed to collect an optical image of the same size. Consequently, there is a need for a faster ultrasound scanner.

SUMMARY OF THE INVENTION

The present invention relates to a device and method of capturing a fingerprint image representing the friction ridge surface of a finger. A platen may be provided and a user may place his finger on the platen in order to permit information to be gathered which may be used to create an image of the fingerprint. A plane pulse-wave generator may generate an ultrasound wave pulse and an ultrasonic wave detector may be used to receive reflected ultrasound signals. The plane pulse-wave generator may be located between the receiving device and the platen.

A phased array of piezoelectric transducer elements can be used to both steer and focus an ultrasound pulse to a target area pixel in a raster scanning process. This may be attractive from a manufacturing perspective in that it may allow the electronic focusing and steering of an ultrasound pulse and avoid the mechanical positioning and alignment required in present ultrasound scanning systems.

In an embodiment of the invention, a platen and a finger may receive ultrasonic wave energy and the reflected energy may be detected and converted to an image of the finger by means of an array of detecting elements. In a line array configuration, information about the fingerprint may be acquired by moving the line array detector and collecting image information one line at a time. A line area detector may be used with a line array generator or an area array generator. A system without moving components may be constructed and the finger may be dragged across the platen to allow the image to be collected. Alternatively, by providing an area array detector and an area array generator, an image may be obtained faster, and the user need not be required to move his finger in order to facilitate image collection.

A fingerprint scanning system is disclosed herein which may be used to measure and image the friction ridge surface of a finger, to obtain an image that is representative of the ridge and valley structure of the skin on the finger. The scanning system may have (a) an imaging surface (sometimes referred to as a platen), which may be a substantially flat piece of polished polycarbonate, that contacts the finger or fingers being imaged, and (b) a device for accurately measuring the relief profile of a skin surface that is in contact with the imaging surface by means of ultrasound transmitting and detecting devices and techniques. It should be noted that the embodiments described in this document are not meant to limit the scope of the invention. Further, each embodiment described in this document may function in either a direct reading mode or as a phased array mode.

BRIEF DESCRIPTION OF THE FIGURES

The invention will now be described by way of non-limiting examples, with reference to the attached drawings and diagrams in which.

FURTHER DESCRIPTION OF THE INVENTION

Figure 1A:
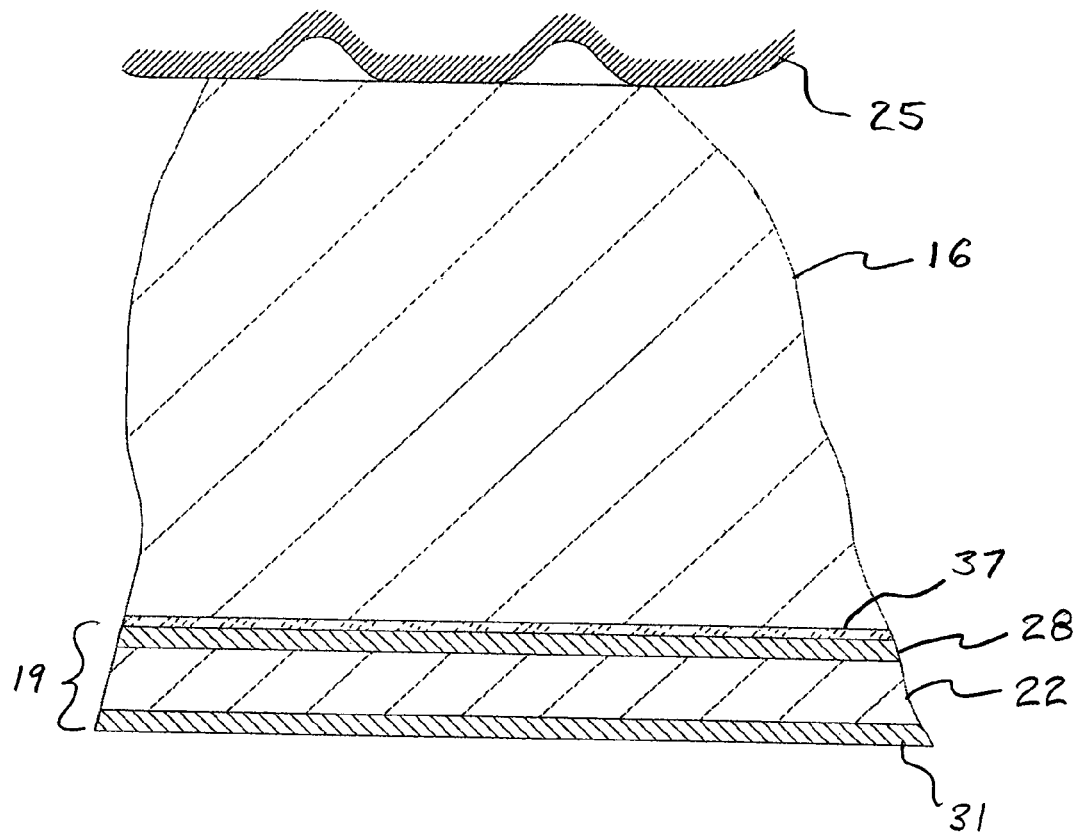
FIG. 1A is a cross-sectional view of a platen and a plane pulse-wave generator according to the invention.

The invention may be embodied as a fingerprint scanner 10. Such a scanner 10 may have an ultrasonic wave detector 13, a platen 16 and an ultrasonic wave generator 19 located between the detector 13 and the platen 16. The generator 19 may include a piezoelectric film 22. Pulse waves may be generated by applying a voltage to the piezoelectric film 22 to expand or contract the film 22, depending upon the charge applied, to generate a plane pulse-wave. The voltage may be applied to the film 22 via a first electrode 28 and a second electrode 31. In this fashion, an ultrasound wave pulse may be made by changing the volume occupied by the film. This pulse-wave travels toward the finger, passes through the platen 16, and is reflected from the finger 25, passes back through the platen 16, through the first electrode 28, film 22, and second electrode 31 until it strikes the detector 13.

The detector 13 and the generator 19 may be separated. A fluidic transmission medium 33 may be located between the detector 13 and the generator 19. Suitable fluidic transmission media 33 may have very different viscosities, relative to each other. For example, one suitable fluidic transmission medium 33 may be mineral oil. Another suitable fluidic transmission medium 33 may be a gel comprised of vinyl plastisol. Using a gel may have an advantage over less viscous transmission media 33 because a gel is less prone to leak out of the scanner 10. For ease of reference, the term "fluidic transmission medium" is used to include many types of materials, including those that are commonly described as gels.

FIG. 1A is a cross-sectional view of an embodiment of the platen 16 and generator 19 according to the invention. The generator 19 may include a piezoelectric film 22, a first metallic electrode layer 28 on a first side of the film, and a second metallic electrode layer 31 on a second side of the film 22. The metallic electrode layers 28, 31 may be sputtered or otherwise attached to the film 22. The generator 19 may be attached to the platen 16 via an adhesive 37, such as an epoxy, a two-part acrylic, or a cyanoacrylate super glue. For example, the first metallic electrode layer 28 may be attached to the platen 16 by an adhesive 37 that resides between the first electrode layer 28 and the platen 16, so as to attach the first electrode layer 28 to the platen 16. In such an embodiment, the platen 16 not only provides a surface on which a finger 25 may be placed, but also protects the generator 19, particularly from things that might damage the generator 19, like fingernails and jewelry.

Figure 1B:
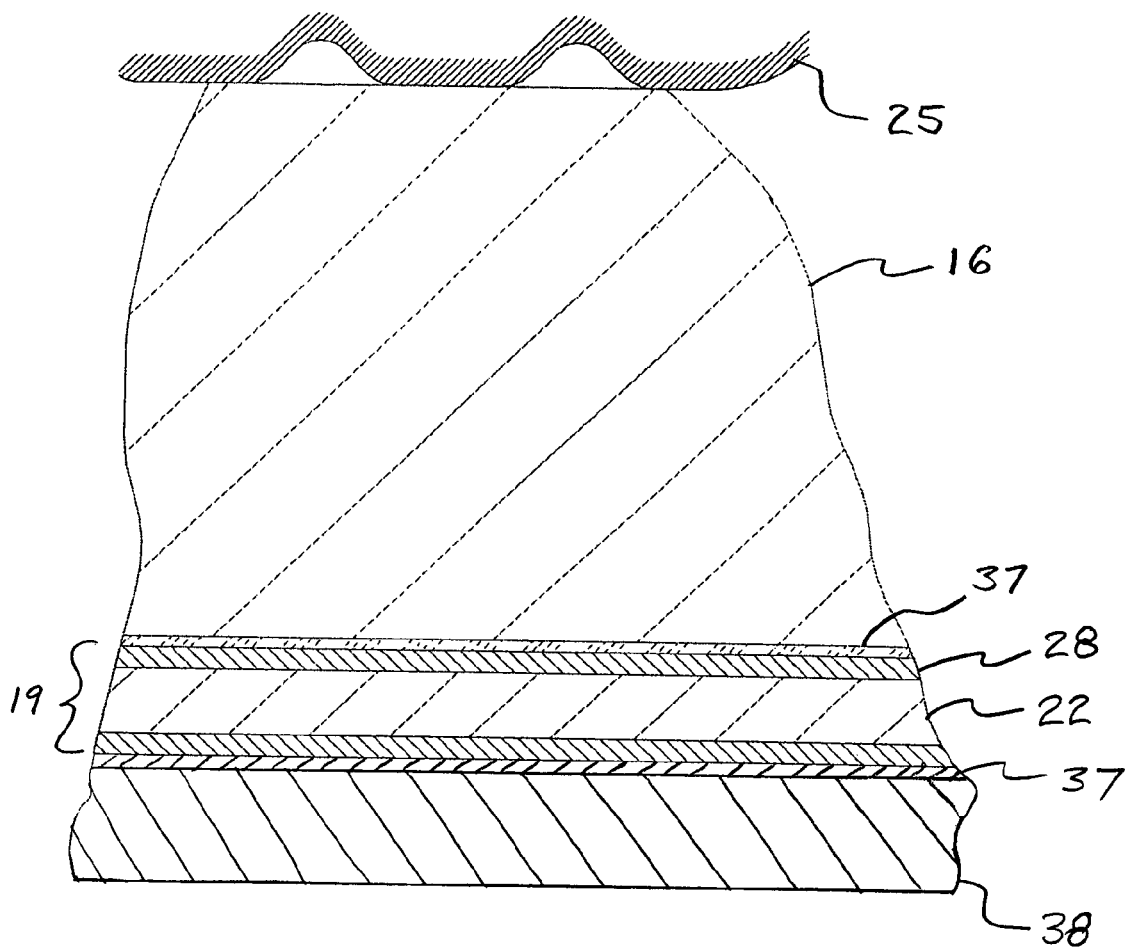
FIG. 1B is similar to FIG. 1A, except a backing plate has been added.

FIG. 1B depicts an embodiment of the invention that is similar to that shown in FIG. 1A. The embodiment of FIG. 1B includes a backing plate 38. The backing plate 38 may be fixed to the second electrode layer 31 by an adhesive 37 that resides between the second electrode layer 31 and the backing plate 38. The backing plate 38 may direct more of the ultrasonic energy from the film 22 toward the finger 25 than in the embodiment of FIG. 1A. The backing plate 38 may be fixed to the platen 16, or the backing plate 38 and the platen 16 may be arranged as an integral piece, thereby embedding the generator 19. The backing plate 38 may be made from the same material as the platen 16.

Figure 1C:
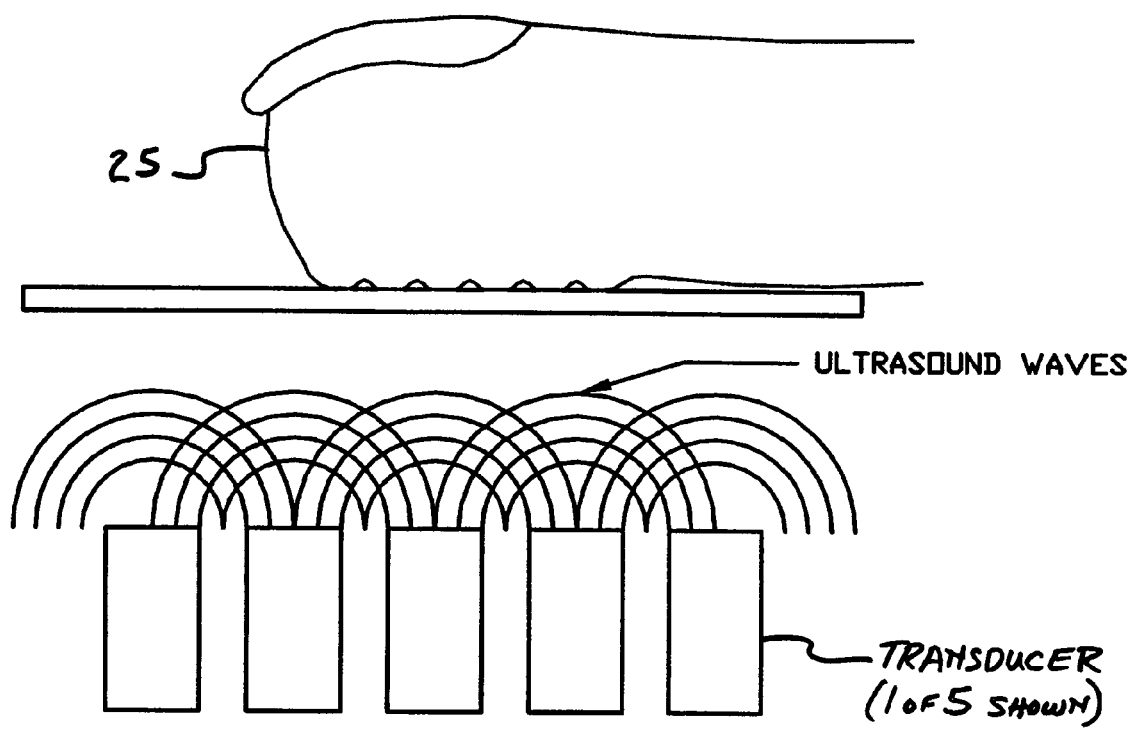
FIG. 1C illustrates a prior art ultrasound device in which discrete transducers are used to send and receive ultrasound waves.

In prior art systems discrete transducer elements are used to both emit and detect an ultrasound pulse. Arrays of these discrete transducer elements are often used, and such arrays create wave interference problems as a result of the discretely generated point sources of the wave pulses. The waves from transducers in the array can intersect and both nullify or amplify each other as they interfere. FIG. 1C depicts a prior art device and illustrates ultrasonic waves emanating from transducer elements. Although the effects of wave interference can be reduced, for example by data manipulation using computer software and/or by including energy absorbing materials between transducer elements, it may be simpler and cheaper to avoid wave interference by generating a plane wave pulse. The devices depicted in FIG. 1A and FIG. 1B are examples of such devices.

Figure 1D:
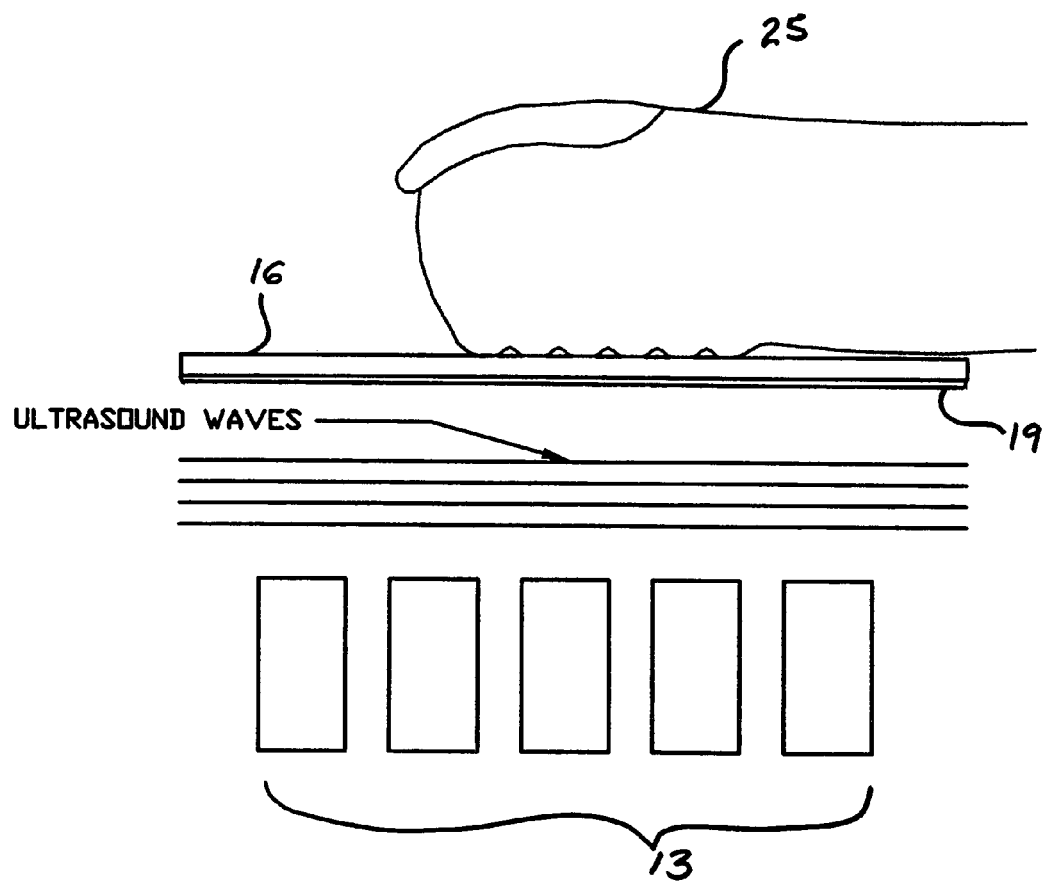
FIG. 1D illustrates plane waves traveling toward a detector comprised of discrete detection elements according to the invention.

Since the piezoelectric film 22 may reside substantially in a plane, the wave generated by the film 22 may be used to generate a wave that emanates in a planar fashion. FIG. 1D illustrates plane waves traveling toward a detector 13 according to the invention. A device that produces a wave that emanates in a planar fashion is generically referred to herein as a "plane pulse-wave generator". Such devices may have a length Lg that is greater than a width Wg, and these generators 19 are generically referred to herein as "line array plane pulse-wave generators." Generators 19 that have a length Lg that is similar to a width Wg are generically referred to herein as "area array plane pulse-wave generators."

An array that might be used in a prior art device for the discrete element transmitter/receiver could be used in the invention as a detector 13. In such an embodiment, the emitter capability of such a transducer would not be used. Additionally, a receive-only array that may be more fragile in construction than the transmit/receive array could also be used. Such arrays, both rugged and fragile types, are available from commercial sources and although not specifically designed for fingerprinting systems are suitable for use in the invention as a detector 13.

Figure 2:
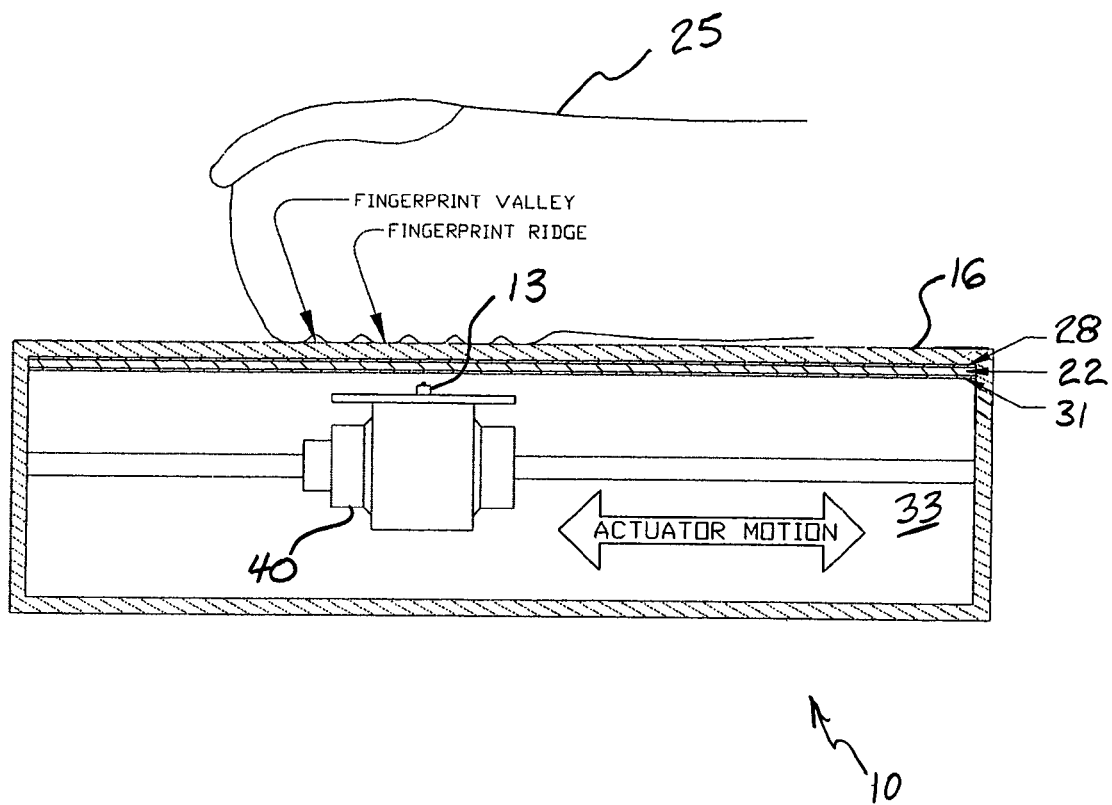
FIG. 2 depicts an embodiment of the invention in which a plane pulse-wave generator is fixed to a platen and a line array ultrasound detector is mounted on a linear actuator.

FIG. 2 is a diagram depicting a fingerprint scanner 10 that utilizes a line array ultrasound detector 13 and a plane pulse-wave generator 19 as the ultrasound source. A line array detector 13 may have a length Ld that is greater than a width Wd of the line array detector 13. For example, the detector 13 may have a width that is only one pixel wide and a length that is more than 50 pixels to provide a length-to-width ratio greater than 50. In one embodiment of the invention, the detector 13 may be attached to a linear actuator 40 so that the detector 13 may be moved in a direction that is substantially perpendicular to the length Ld of the detector 13 so as to gather information about different locations along a finger 25 that is being imaged. The detector 13 may be moved in a plane that is substantially parallel to the platen 16, or substantially parallel to the generator 19, or both. By linearly translating the detector 13 relative to the platen 16 surface, the detector 13 may collect image information about the fingerprint at different locations, one line at a time. The plane pulse-wave generator 19 may generate an ultrasound pulse as the line array detector 13 advances, and with each pulse generated, a line of image information may be collected by the detector 13. The space between the generator 19 and the detector 13 may be filled with a fluidic ultrasound transmission medium 33 such as mineral oil.

Figure 3:
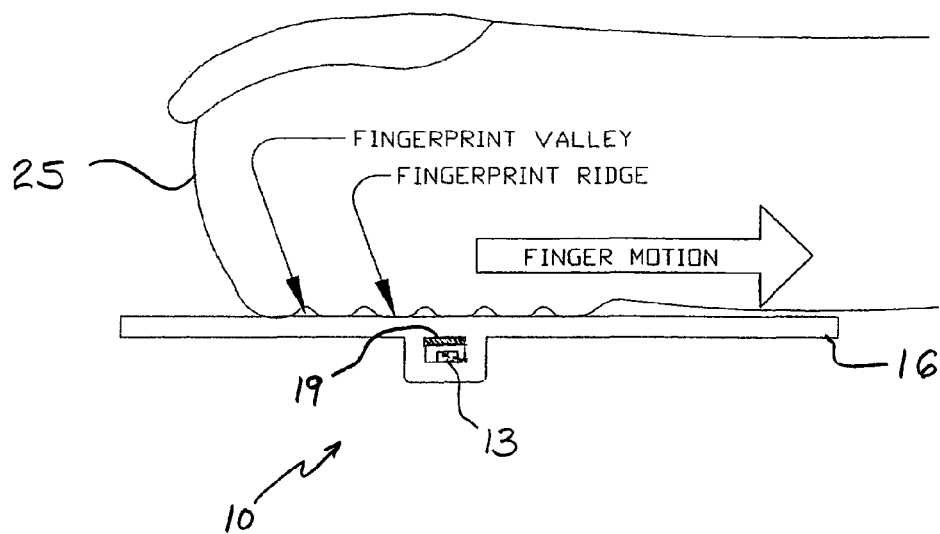
FIG. 3 depicts an embodiment of the invention in which the plane pulse-wave generator and a line array detector are fixed to the platen surface.
Figure 4:
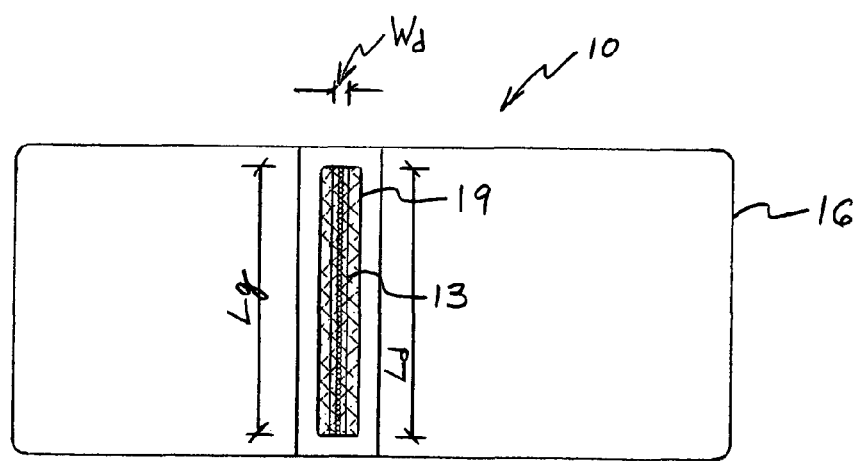
FIG. 4 is a bottom view of the embodiment illustrated in FIG. 3.

The embodiment shown in FIG. 3 operates in a manner similar to that of FIG. 2, but there are no mechanical moving parts in the embodiment depicted in FIG. 3. The user moves his finger 25 over the platen 16 at an image line of the detector 13. Scanning may be accomplished by acquiring one line at a time of image information as the finger 25 is dragged across the platen 16. Motion of the finger 25 may be determined optically or by ultrasound using Doppler shift measurements, and emission of plane pulse-waves by the generator 19 may be synchronized with the motion of the finger 25. FIG. 4 shows the device of FIG. 3 from the bottom.

Figure 5:
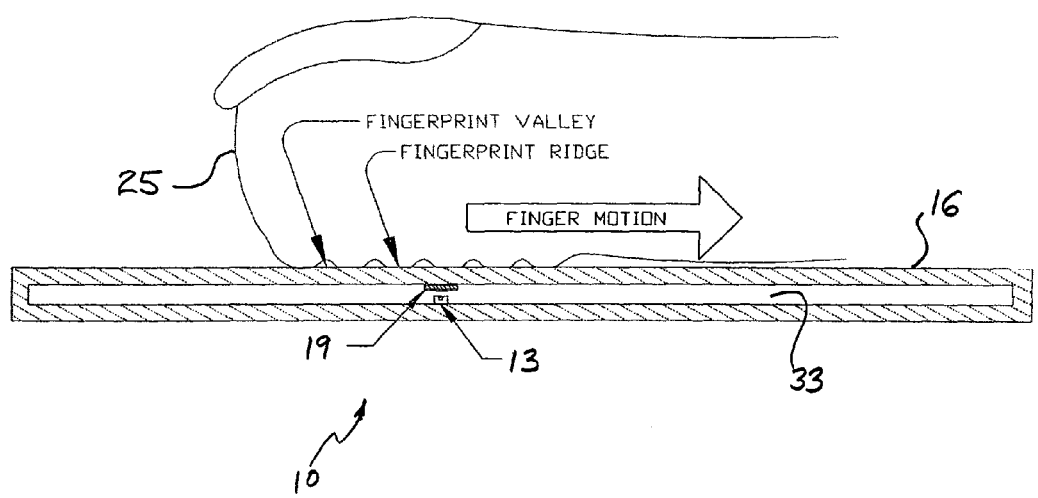
FIG. 5 depicts an embodiment of the invention that is similar to that depicted in FIG. 3, except the line array detector is spaced apart from the plane pulse-wave generator.

FIG. 5 shows an embodiment similar to FIG. 3, except that the line array detector 13 is spaced apart from the pulse plane-wave generator 19. The space between the detector 13 and the generator 19 may be filled with a fluidic transmission medium 33.

The embodiment of FIG. 3, FIG. 4 and FIG. 5 may introduce distortions in the skin caused by the dragging operation. However, it is believe such distortions should be minor. The information from the detector 13 may be electronically altered in order to compensate for expected errors so that the image does not include the distortions, or so as to reduce the distortions. Alternatively, the distortions may be included as an error in the image.

Figure 6:
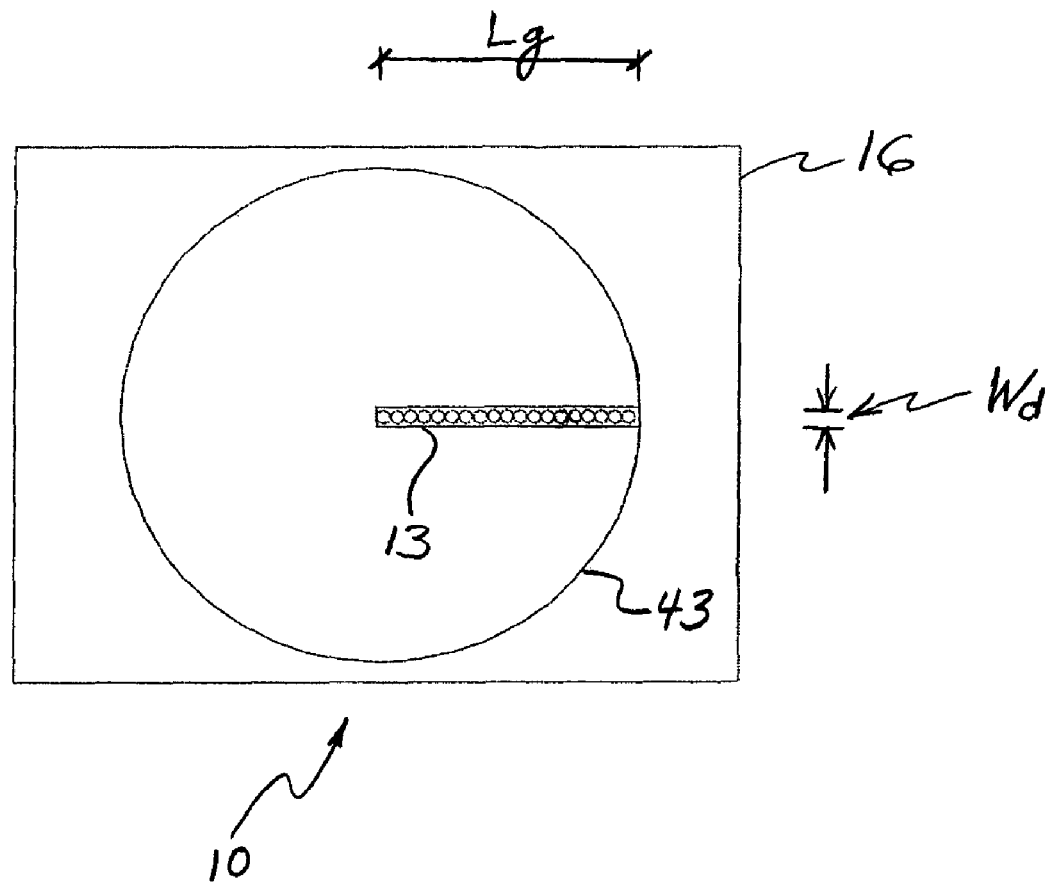
FIG. 6 depicts a platen and a line array ultrasound detector mounted on a flywheel that is capable of rotating in an angular fashion.
Figure 7:
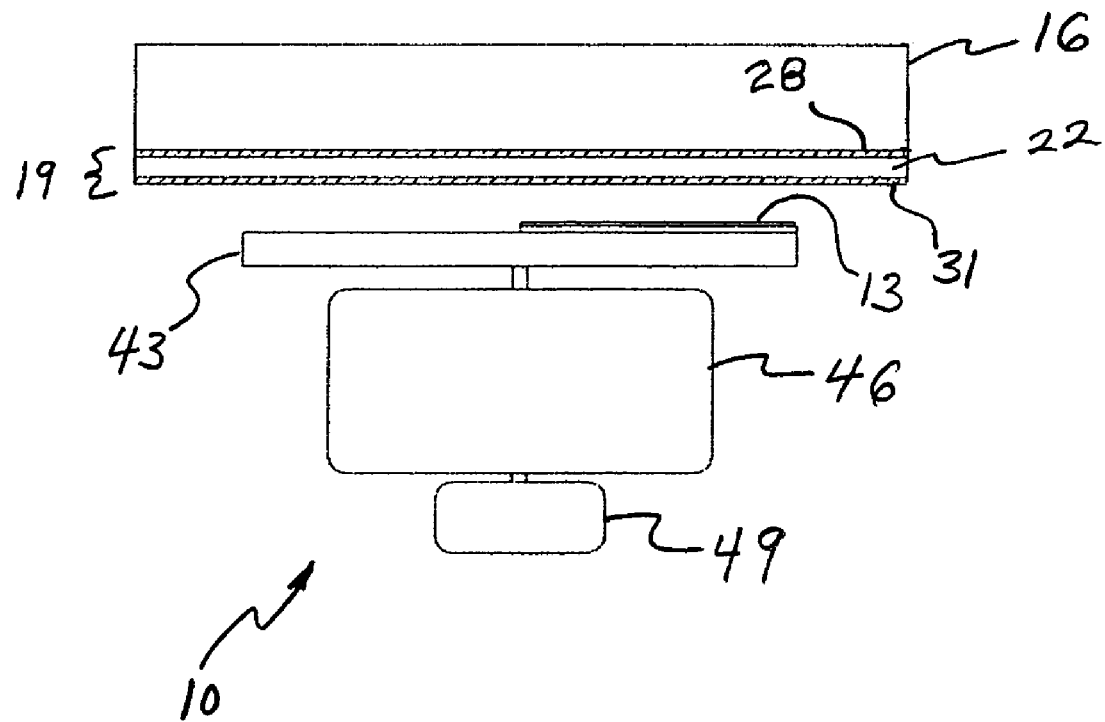
FIG. 7 is a side view of the arrangement shown in FIG. 6.

FIG. 6 and FIG. 7 show an embodiment of the invention having a line array detector 13 mounted on a rotatable wheel 43. A plane pulse-wave generator 19 may be located between the platen 16 and the detector 13. A motor 46 may be used to rotate the wheel 43. A position monitoring device may be included and used to monitor the position of the detector 13, for example, by monitoring the wheel's position. Suitable position monitoring devices may include a rotary optical encoder 49 and code wheel, resolver, or simply by timing pulses in a constant angular velocity system.

The wheel 43 may be rotated so as to move the line array detector 13 in an angular fashion in a plane that is substantially parallel to the platen 16. In this embodiment, the detector 13 may be angularly swept in a circle in order to gather data about the finger 25. While sweeping in an angular fashion, the detector 13 may be moved in a plane that is substantially parallel to the platen 16, or substantially parallel to the generator 19, or both.

Figure 8:
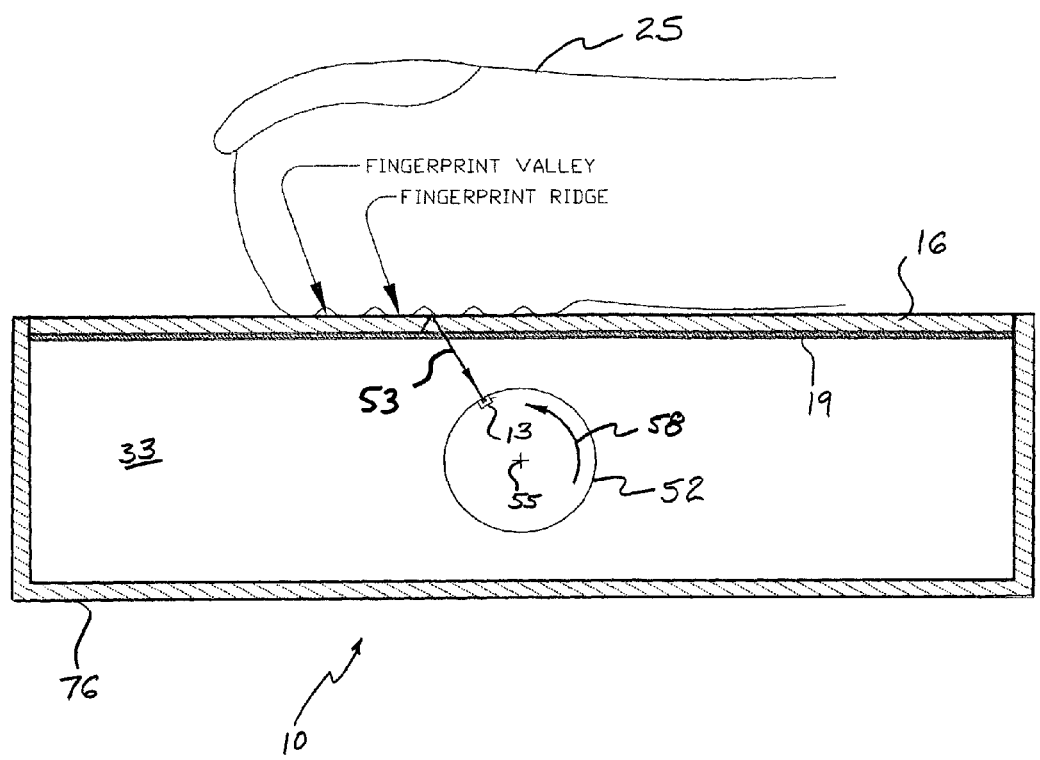
FIG. 8 depicts an arrangement according to the invention in which a line array ultrasound detector is mounted on a cylinder that is capable of oscillating in order to move the detector in an arcuate fashion.

FIG. 8 depicts another embodiment of the invention, which has a line array ultrasound detector 13 mounted to a cylinder 52. The arrow 53 identifies a path that the ultrasound pulse may take as it travels from the generator 19 to the detector 13. The cylinder 52 may be capable of oscillating about an axis of rotation 55 that is substantially parallel to the platen 16, and thereby is capable of causing the detector 13 to move arcuately. The arrow 58 identifies one direction in which the cylinder 52 may rotate, but it should be understood that the invention may be implemented in a manner wherein the cylinder 52 arcuately moves back and forth so that the detector 13 is always able to receive reflected ultrasound pulses. The axis of rotation 55 about which the detector 13 moves may be oriented to be substantially parallel to the platen 16 surface so that the distance between the detector 13 and the platen 16 is substantially constant across the length of the detector 13 for a particular arcuate position of the cylinder 52. The axis of rotation 55 may be substantially parallel to the generator 19, or both the platen 16 and the generator 19.

Figure 9:
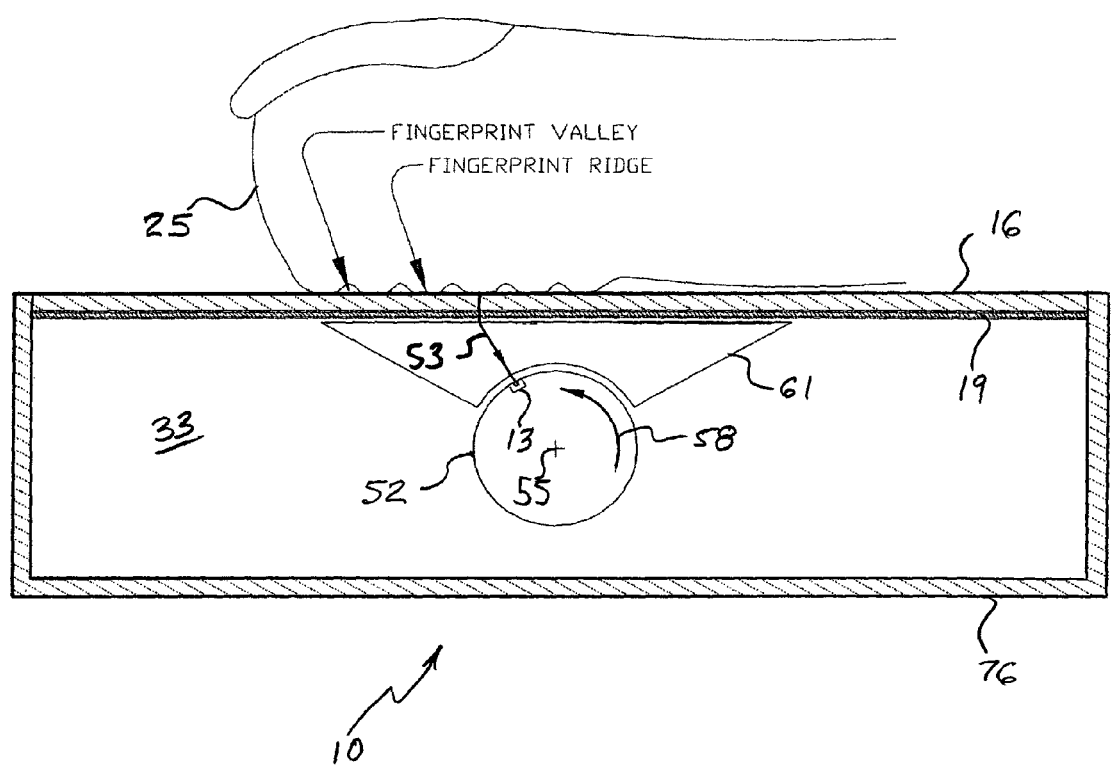
FIG. 9 depicts an embodiment of the invention that is similar to that shown in FIG. 8, except the arrangement in FIG. 9 includes a Fresnel surface located between the plane pulse-wave generator and the detector.
Figure 10:
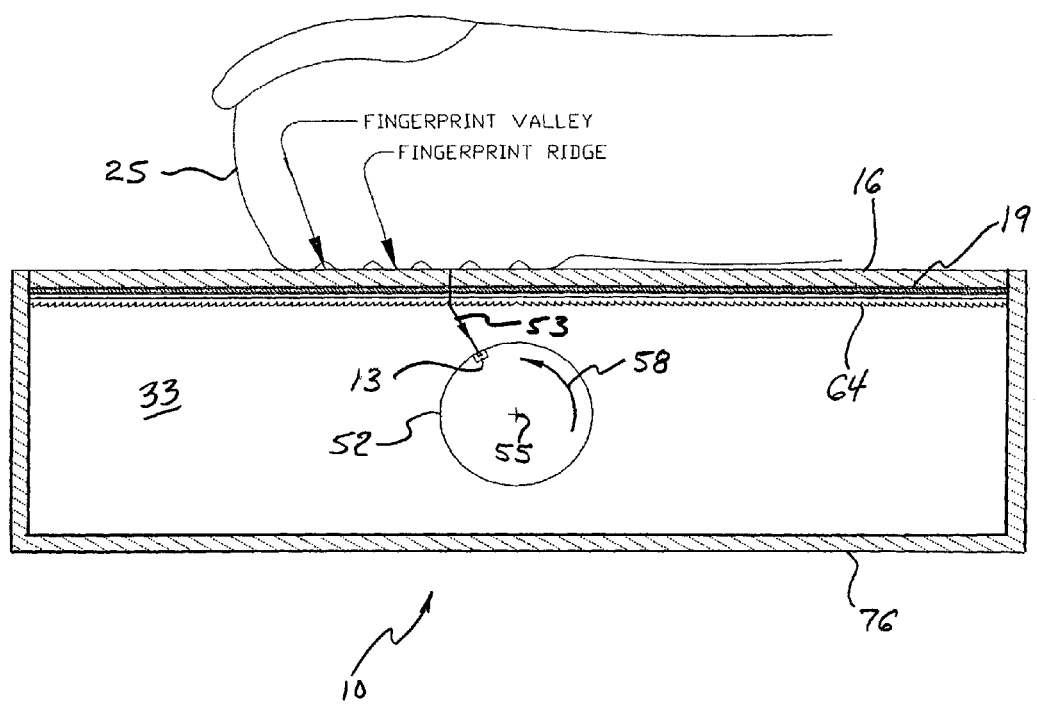
FIG. 10 depicts an embodiment of the invention that is similar to that shown in FIG. 9, except that a Fresnel grating is used.
Figure 11A:
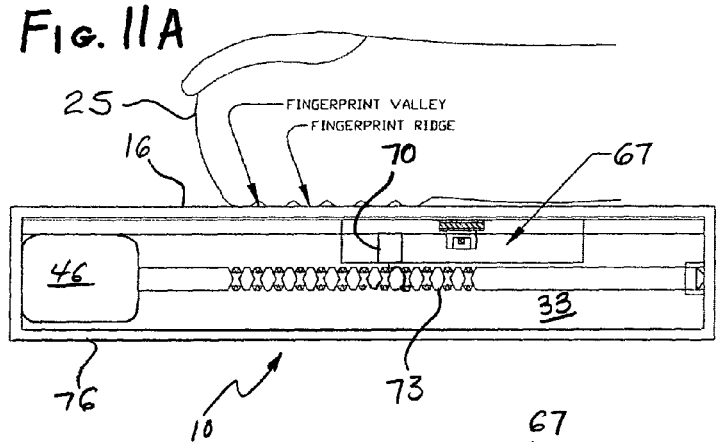
FIGS. 11A, 11B and 11C are side, bottom and end views of an embodiment of the invention that includes a line array plane pulse-wave generator and a line array ultrasound detector that are both mounted on a moveable carriage.
Figure 11D:
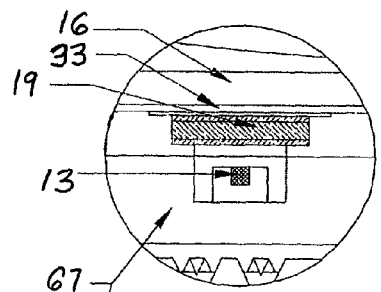
FIG. 11D is an enlarged view of a portion of FIG. 11A.
Figure 11C:
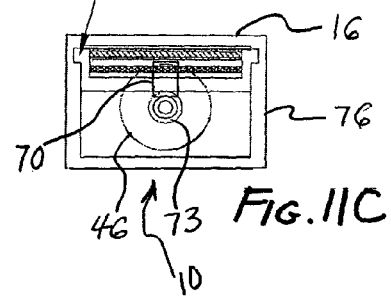
Figure 11B:
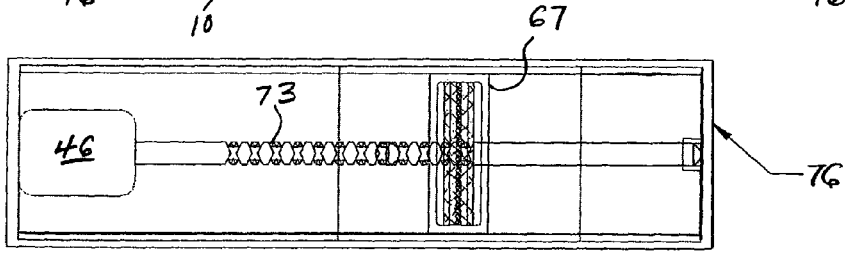

The embodiment shown in FIG. 9 is similar to that of FIG. 8, but uses a prism 61 with a Fresnel surface to better direct the reflected pulses. This system may offer less signal loss than the embodiment depicted in FIG. 8 since the ultrasound pulse exits the prism 61 toward the detector 13 in a substantially perpendicular manner, thereby minimizing the amount of energy reflected within the prism 61. The embodiment shown in FIG. 10 is similar to that in FIG. 9 but uses a cylindrical Fresnel grating 64 instead of a prism 61. The Fresnel grating may be less expensive to manufacture than the prism.

FIGS. 11A, 11B, 11C and 11D depict a fingerprint scanner 10 having a platen 16 and a movable carriage 67. The carriage 67 may have a cam follower 70 that engages a worm cam 73, and the worm cam 73 may be turned via a motor 46. By turning the worm cam 73, the carriage 67 is caused to move from one end of the housing 76 to another end of the housing 76.

The carriage 67 may have mounted thereon a line array ultrasound detector 13 and a plane pulse-wave generator 19. The generator 19 may have a width that is only one pixel wide and a length that is more than 50 pixels, to provide a length-to-width ratio greater than 50. The carriage 67 may be translated near the platen 16 and submerged in a fluidic ultrasound transmitting medium 33, such as mineral oil. Such a system may be programmed to acquire image information in either or both, directions of travel.

Figure 12:
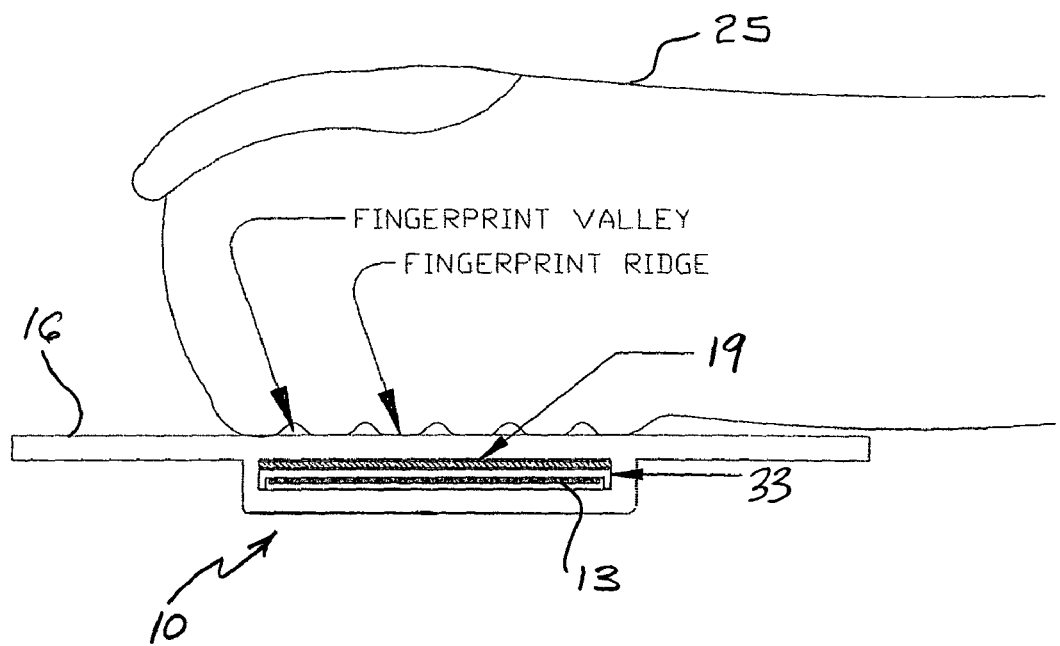
FIG. 12 depicts an embodiment of the invention which includes an area array plane pulse-wave generator and an area array ultrasound detector.
Figure 13:
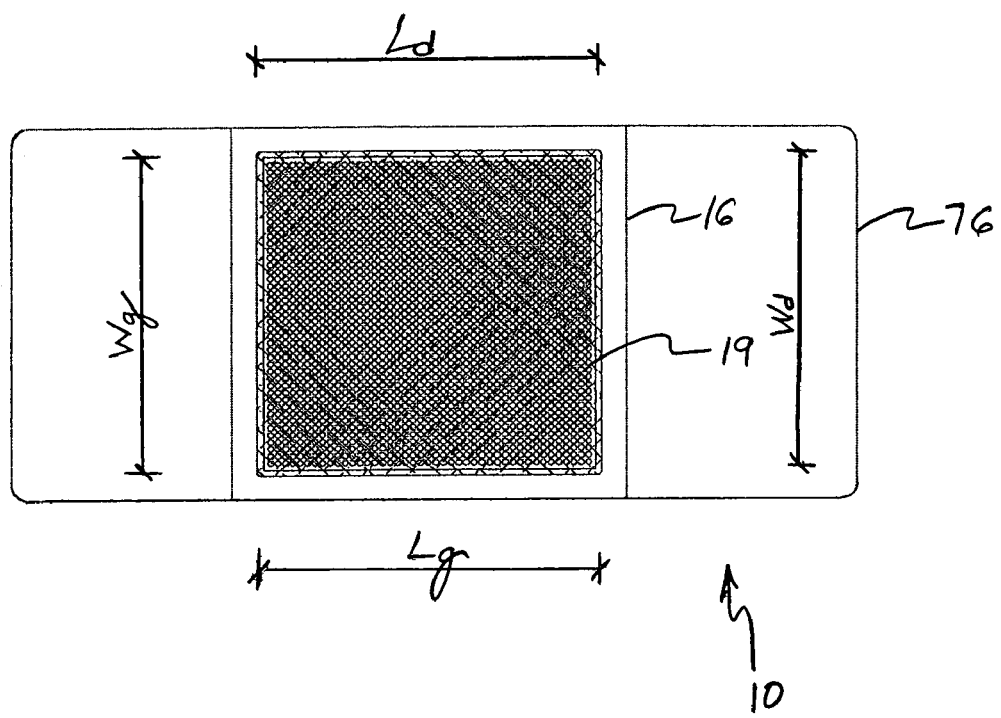
FIG. 13 is a bottom view of the device depicted in FIG. 12.

FIG. 12 and FIG. 13 show a finger scanner 10 according to the invention. An area array ultrasound detector 13 and an area array ultrasound plane pulse-wave generator 19 are shown. In an area array detector 13, a length Ld of the detector 13 is similar to a width of the detector 13. The subject's finger 25 may be placed on the platen 16, a pulse may be generated by the plane pulse-wave generator 19, and each pixel element of the area array detector 13 may detect a single pixel of image information from the pulse echo. In this embodiment of the invention, the surface of the finger 25 that is in contact with the platen 16 may be imaged in a single event without the need for the user to drag his finger 25 across the platen 16. In this embodiment, there are no fingerprint distortion effects as would be the case in the embodiment of FIG. 3 or FIG. 5.

It should be noted that the embodiments of FIG. 3, FIG. 4, FIG. 5, FIG. 11 and FIG. 12 illustrate how the invention might be implemented so that the position of the detector 13 and a position of the generator 19 are fixed relative to each other. FIG. 11 depicts an arrangement in which the detector 13 and the generator 19 move while the finger 25 to be imaged remains stationary in order to gather information about the finger 25. In that arrangement, the detector 13 and the generator 19 may be linearly movable in a plane that is substantially parallel to the platen 16. In such an embodiment, the distance between the generator 19 and the platen 16 may be substantially fixed across the range of movement of the generator 19. By contrast, the embodiments of FIG. 3, FIG. 4, and FIG. 5 contemplate movement of the finger 25 across the platen 16. In this manner, the generator 19 and the detector 13 may be stationary. Such an embodiment of the invention has the advantage of using relatively fewer moving parts, which should translate into lower maintenance costs and greater reliability. FIG. 12 has the advantage that the generator 19 and the detector 13 may be stationary, and movement of the finger 25 is not required. The arrangement of FIG. 12 should provide a system having lower maintenance costs, greater reliability and fewer image distortions.

Figure 14:
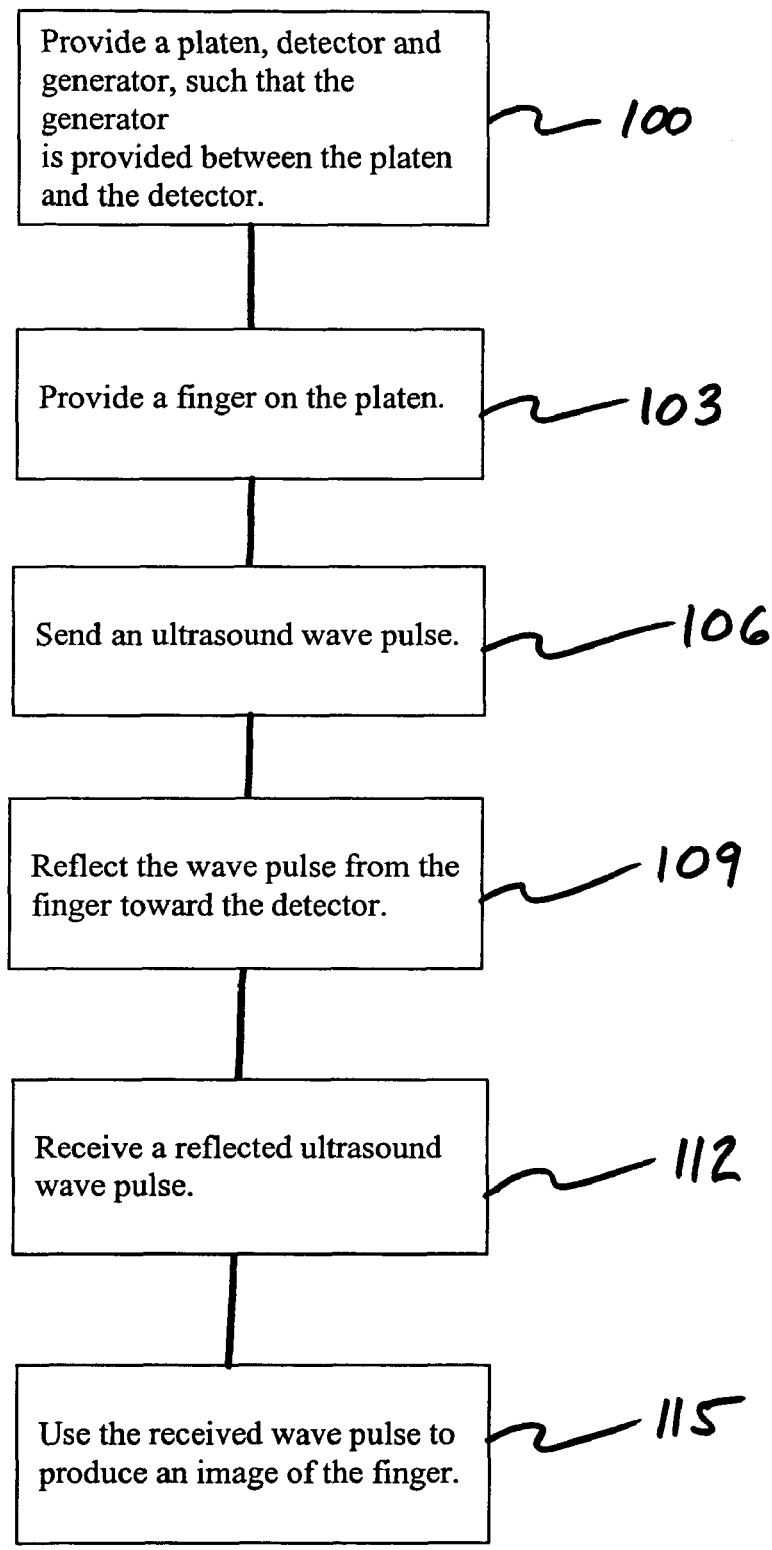
FIG. 14 depicts a method according to the invention.

The invention may be embodied as a method. FIG. 14 depicts one such method in which a platen, detector and generator may be provided 100. The generator may be provided between the platen and the detector. A finger may be provided 103 on the platen. An ultrasound wave pulse may be sent 106 from the generator toward the finger. The wave pulse may be reflected 109 from the finger toward to the detector. The reflected ultrasound wave pulse may be received 112 from the finger, and the received wave pulse may be used 115 to produce an image of the finger.

The method may be carried out such that sending the ultrasound wave pulse includes expanding a film, such as the piezoelectric film described above. In such a method, the film may be expanded by applying a voltage difference across the film.

The detector may be moved relative to the platen in order to receive reflected ultrasound wave pulses from different parts of the finger. In this manner, information about different parts of the finger may be gathered by the detector and used to produce an image of the finger. For example, the detector may be moved angularly in a plane that is substantially parallel to the platen. In another embodiment of the invention, the detector may be moved arcuately about an axis that is parallel to the platen. The detector may also be moved linearly.

U.S. provisional patent application No. 60/616,953 includes descriptions of embodiments according to the invention. Application 60/616,953 is incorporated herein by reference.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A fingerprint scanner, comprising:
an ultrasonic wave detector;
a platen; and
an ultrasonic wave generator located between the detector and the platen, wherein the generator has a length-to-width ratio greater than 50.

2. The scanner of claim 1, wherein the generator is an area-array generator.

3. The scanner of claim 1, wherein the generator is a line-array generator.

4. The scanner of claim 1, wherein the generator includes a piezoelectric film.

5. The scanner of claim 4, wherein the generator includes a first electrode layer on a first side of the film, and a second electrode layer on a second side of the film.

6. The scanner of claim 5, wherein the first electrode layer is attached to the platen.

7. The scanner of claim 6, wherein an adhesive resides between the first electrode layer and the platen and serves to attach the first electrode layer to the platen.

8. The scanner of claim 5, further comprising a backing plate attached to the second electrode layer.

9. The scanner of claim 8, wherein an adhesive resides between the second electrode layer and the backing plate and serves to attach the second electrode layer to the backing plate.

10. The scanner of claim 1, further comprising a linear actuator attached to the detector.

11. The scanner of claim 1, further comprising a fluidic transmission medium located between the detector and the generator.

12. The scanner of claim 1, further comprising a gel transmission medium located between the detector and the generator.

13. The scanner of claim 1, wherein the detector is arranged as a line array.

14. The scanner of claim 13, the detector has a length-to-width ratio greater than 50.

15. The scanner of claim 14, wherein the detector is movable in a direction that is substantially perpendicular to a length of the detector.

16. The scanner of claim 13, wherein the line array is angularly movable in a plane that is substantially parallel to the platen.

17. The scanner of claim 13, wherein the line array is angularly movable in a plane that is substantially parallel to the generator.

18. The scanner of claim 13, wherein the line array is linearly movable in a plane that is substantially parallel to the platen.

19. The scanner of claim 13, wherein the line array is linearly movable in a plane that is substantially parallel to the generator.

20. The scanner of claim 13, wherein the line array is arcuately movable.

21. The scanner of claim 20, wherein the line array is arcuately movable about an axis of rotation that is substantially parallel to the platen.

22. The scanner of claim 20, wherein the line array is arcuately movable about an axis of rotation that is substantially parallel to the generator.

23. The scanner of claim 20, further comprising a Fresnel surface capable of guiding toward the detector ultrasonic waves reflected from a finger.

24. The scanner of claim 23, wherein the refracted ultrasonic waves are those that have been reflected by the finger substantially back upon a path of unreflected ultrasonic waves.

25. The scanner of claim 23, wherein the Fresnel surface is a Fresnel grating.

26. The scanner of claim 1, wherein the detector is arranged as an area array.

27. The scanner of claim 1, wherein a position of the detector and a position of the generator are fixed relative to each other.

28. The scanner of claim 27, wherein the detector and the generator are linearly movable in a plane that is substantially parallel to the platen.

29. The scanner of claim 28, wherein a distance between the generator and the platen is substantially fixed.

30. The scanner of claim 29, wherein the platen permits movement of a finger.

31. A method of scanning a finger, comprising:
providing a platen;
providing a detector;
providing a generator between the platen and the detector, wherein the generator has a length-to-width ratio greater than 50;
providing a finger on the platen;
sending an ultrasound wave pulse from the generator toward the finger;
receiving a reflected ultrasound wave pulse from the finger; and
using the received reflected ultrasound wave pulse to produce an image of the finger.

32. The method of claim 31, wherein the generator includes a film, and sending an ultrasound wave pulse includes changing the volume occupied by the film.

33. The method of claim 32, wherein the film volume is changed by applying a voltage difference across the film.

34. The method of claim 31, further comprising moving the detector relative to the platen in order to receive reflected ultrasound wave pulses from different parts of the finger.

35. The method of claim 34, wherein the detector is moved angularly.

36. The method of claim 34, wherein the detector is moved arcuately.

37. The method of claim 34, wherein the detector is moved linearly.

38. A fingerprint scanner, comprising:
an ultrasonic wave detector, wherein the detector is arranged as a line array;
a platen; and
an ultrasonic wave generator located between the detector and the platen.

39. The scanner of claim 38, wherein the generator is an area-array generator.

40. The scanner of claim 38, wherein the generator is a line-array generator.

41. The scanner of claim 40, wherein the generator has a length-to-width ratio greater than 50.

42. The scanner of claim 38, wherein the generator includes a piezoelectric film.

43. The scanner of claim 42, wherein the generator includes a first electrode layer on a first side of the film, and a second electrode layer on a second side of the film.

44. The scanner of claim 43, wherein the first electrode layer is attached to the platen.

45. The scanner of claim 44, wherein an adhesive resides between the first electrode layer and the platen and serves to attach the first electrode layer to the platen.

46. The scanner of claim 43, further comprising a backing plate attached to the second electrode layer.

47. The scanner of claim 46, wherein an adhesive resides between the second electrode layer and the backing plate and serves to attach the second electrode layer to the backing plate.

48. The scanner of claim 38, further comprising a linear actuator attached to the detector.

49. The scanner of claim 38, further comprising a fluidic transmission medium located between the detector and the generator.

50. The scanner of claim 38, further comprising a gel transmission medium located between the detector and the generator.

51. The scanner of claim 38, the detector has a length-to-width ratio greater than 50.

52. The scanner of claim 51, wherein the detector is movable in a direction that is substantially perpendicular to a length of the detector.

53. The scanner of claim 38, wherein the line array is angularly movable in a plane that is substantially parallel to the platen.

54. The scanner of claim 38, wherein the line array is angularly movable in a plane that is substantially parallel to the generator.

55. The scanner of claim 38, wherein the line array is linearly movable in a plane that is substantially parallel to the platen.

56. The scanner of claim 38, wherein the line array is linearly movable in a plane that is substantially parallel to the generator.

57. The scanner of claim 38, wherein the line array is arcuately movable.

58. The scanner of claim 57, wherein the line array is arcuately movable about an axis of rotation that is substantially parallel to the platen.

59. The scanner of claim 57, wherein the line array is arcuately movable about an axis of rotation that is substantially parallel to the generator.

60. The scanner of claim 57, further comprising a Fresnel surface capable of guiding toward the detector ultrasonic waves reflected from a finger.

61. The scanner of claim 60, wherein the refracted ultrasonic waves are those that have been reflected by the finger substantially back upon a path of unreflected ultrasonic waves.

62. The scanner of claim 60, wherein the Fresnel surface is a Fresnel grating.

63. The scanner of claim 38, wherein the detector is arranged as an area array.

64. The scanner of claim 38, wherein a position of the detector and a position of the generator are fixed relative to each other.

65. The scanner of claim 64, wherein the detector and the generator are linearly movable in a plane that is substantially parallel to the platen.

66. The scanner of claim 65, wherein a distance between the generator and the platen is substantially fixed.

67. The scanner of claim 66, wherein the platen permits movement of a finger.

68. A method of scanning a finger, comprising:
  providing a platen;
  providing a detector, wherein the detector is arranged as a line array;
  providing a generator between the platen and the detector;
  providing a finger on the platen;
  sending an ultrasound wave pulse from the generator toward the finger;
  receiving a reflected ultrasound wave pulse from the finger; and
  using the received reflected ultrasound wave pulse to produce an image of the finger.

69. The method of claim 68, wherein the generator includes a film, and sending an ultrasound wave pulse includes changing the volume occupied by the film.

70. The method of claim 69, wherein the film volume is changed by applying a voltage difference across the film.

71. The method of claim 68, further comprising moving the detector relative to the platen in order to receive reflected ultrasound wave pulses from different parts of the finger.

72. The method of claim 71, wherein the detector is moved angularly.

73. The method of claim 71, wherein the detector is moved arcuately.

74. The method of claim 71, wherein the detector is moved linearly.

* * * * *